United States Patent [19]

Krämer et al.

[11] Patent Number: 5,294,633

[45] Date of Patent: Mar. 15, 1994

[54] IMIDAZOLYL-PROPENOIC ACID DERIVATIVES

[75] Inventors: Thomas Krämer; Jürgen Dressel, both of Wuppertal; Rudolf Hanko, Essen; Walter Hübsch, Wuppertal; Ulrich Müller, Wuppertal; Matthias Müller-Gliemann, Wuppertal; Martin Beuck, Erkrath; Stanislav Kazda; Johannes-Peter Stasch, both of Wuppertal; Andreas Knorr, Erkrath; Stefan Wohlfeil, Hilden, all of Fed. Rep. of Germany

[73] Assignee: Bayer Aktiengesellschaft, Leverkusen, Fed. Rep. of Germany

[21] Appl. No.: 947,869

[22] Filed: Sep. 21, 1992

[30] Foreign Application Priority Data

Oct. 1, 1991 [DE] Fed. Rep. of Germany ....... 4132631

[51] Int. Cl.$^5$ .................. C07D 25/04; A61K 31/41
[52] U.S. Cl. ...................................... 514/381; 548/253
[58] Field of Search .......................... 548/253; 514/381

[56] References Cited

U.S. PATENT DOCUMENTS

| 5,128,355 | 7/1992 | Carini et al. | 548/253 X |
| 5,138,069 | 8/1992 | Carini et al. | 548/253 X |
| 5,153,197 | 10/1992 | Carini et al. | 548/253 X |
| 5,155,118 | 10/1992 | Carini et al. | 548/253 X |

FOREIGN PATENT DOCUMENTS

| 0403158 | 6/1990 | European Pat. Off. . |
| 0403159 | 6/1990 | European Pat. Off. . |
| 0425211 | 10/1990 | European Pat. Off. . |
| 9100277 | 1/1991 | World Int. Prop. O. . |
| 9100281 | 1/1991 | World Int. Prop. O. . |

Primary Examiner—David B. Springer
Attorney, Agent, or Firm—Sprung Horn Kramer & Woods

[57] ABSTRACT

Imidazolyl-propenoic acid derivatives can be prepared by reaction of aldehydes with phosphonoacetic acid esters. The imidazolyl-propenoic acid derivatives are suitable as active substances in medicaments, in particular in hypotensive and anti-atherosclerotic medicaments.

9 Claims, No Drawings

IMIDAZOLYL-PROPENOIC ACID DERIVATIVES

The invention relates to imidazolyl-propenoic acid derivatives, to a process for their preparation and to their use as hypotensive and anti-atherosclerotic agents.

It is known that renin, a proteolytic enzyme, eliminates from angiotenbinogen in vivo the decapeptide angiotensin I, which is in turn degraded in the lungs, the kidneys or other tissues to give the hypertensive octapeptide angiotensin II. The various effects of angiotensin II, such as, for example, vasoconstriction, $Na^+$ retention in the kidneys, aldosterone release in the adrenal gland and increase in tone of the sympathetic nervous system, act synergistically in the sense of a blood pressure increase.

Moreover, angiotensin II has the property of promoting the growth and the replication of cells such as, for example, of cardiac muscle cells and smooth muscle cells, these growing and proliferating in an increased manner in various disease states (for example hypertension, atherosclerosis and cardiac insufficiency).

In addition to the inhibition of renin activity, a possible starting point for intervention in the renin-angiotensin system (RAS) is the inhibition of the activity of angiotensin-converting enzyme (ACE) and the blockade of angiotensin II receptors.

In the publications EP 324,377, EP 403,158 and EP 403,159, imidazoles are described in which the scope of meaning of position 2 (see compounds according to the invention —CH=CH—$CO_2R^3$) encompasses propenoic acids and esters and the terminal phenyl ring is substituted by a tetrazole ring, but without giving a reference to an actual substance representative of this substitution pattern.

Substituted imidazoles whose 2-position is substituted by a propenoic acid or ester group and whose terminal phenyl rings are substituted by a tetrazole ring have now been found which have surprisingly good A-II antagonistic action.

The invention relates to imidazolyl-propenoic acid derivatives of the general formula (I)

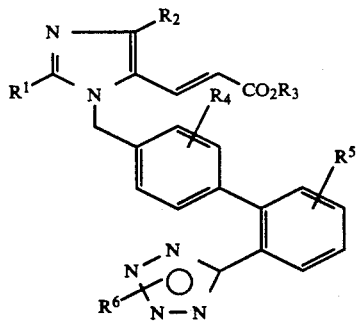

in which
$R^1$ represents straight-chain or branched alkyl or alkenyl each having up to 8 carbon atoms, each of which is optionally substituted by cycloalkyl having 3 to 6 carbon atoms, or represents cycloalkyl having 3 to 8 carbon atoms,
$R^2$ represents hydrogen, halogen, hydroxyl, nitro, cyano, trifluoromethyl, trifluoromethoxy or pentafluoroethyl, or represents straight-chain or branched alkyl having up to 6 carbon atoms, or represents aryl having 6 to 10 carbon atoms,
$R^3$ represents hydrogen, straight-chain or branched alkyl having up to 8 carbon atoms or phenyl,
$R^4$ and $R^5$ are identical or different and represent hydrogen, halogen, cyano, nitro, trifluoromethyl, hydroxyl, trifluoromethoxy or straight-chain or branched alkyl or alkoxy each having up to 6 carbon atoms,
$R^6$ represents hydrogen or straight-chain or branched alkyl having up to 6 carbon atoms
and their salts.

The imidazolyl-propenoic acid derivatives according to the invention can also be present in the form of their salts. In general, salts with organic or inorganic bases or acids may be mentioned here.

In the context of the present invention, physiologically acceptable salts are preferred. Physiologically acceptable salts of the imidazolyl-propenoic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. The racemic forms, like the diastereomers, can be separated in a known manner into the stereoisomerically uniform constituents [cf. E. L. Eliel, Stereochemistry of Carbon Compounds, McGraw Hill, 1962].

Preferred compounds of the general formula (I) are those in which
$R^1$ represents straight-chain or branched alkyl or alkenyl each having up to 6 carbon atoms, each of which is optionally substituted by cyclopropyl, cyclobutyl, cyclopentyl or cyclohexyl, or represents cyclopropyl, cyclopentyl or cyclohexyl,
$R^2$ represents hydrogen, fluorine, chlorine, bromine, iodine, trifluoromethyl, trifluoromethoxy, pentafluoroethyl, phenyl or straight-chain or branched alkyl having up to 6 carbon atoms,
$R^3$ represents hydrogen or straight-chain or branched alkyl having up to 6 carbon atoms,
$R^4$ and $R^5$ are identical or different and represent hydrogen, fluorine, chlorine, bromine, trifluoromethyl, trifluoromethoxy or straight-chain or branched alkyl having up to 4 carbon atoms,
$R^6$ represents hydrogen or straight-chain or branched alkyl having up to 4 carbon atoms
and their salts.

Particularly preferred compounds of the general formula (I) are those in which $R^1$ represents straight-chain or branched alkyl or alkenyl each having up to 4 carbon atoms, or cyclopropyl, $R^2$ represents hydrogen, fluorine, chlorine, bromine, iodine, trifluoromethyl, pentafluoroethyl, phenyl or straight-chain or branched alkyl having up to 4 carbon atoms, $R^3$ represents hydrogen or straight-chain or branched alkyl having up to 4 carbon atoms, $R^4$ and $R^5$ are identical or different and represent hydrogen, fluorine, chlorine or bromine, $R^6$ represents hydrogen, methyl, ethyl, isopropyl or propyl and their salts.

Very particularly preferred compounds of the general formula (I) are those in which $R^1$ represents straight-chain or branched alkyl or alkenyl each having up to 4 carbon atoms, $R^2$ represents hydrogen, fluorine, chlorine, iodine, trifluoromethyl or pentafluoroethyl, $R^3$ represents hydrogen, methyl or ethyl and $R^4$, $R^5$ and $R^6$ represent hydrogen and their salts.

In addition, a process for the preparation of the compounds of the general formula (I) according to the invention and their salts has been found, characterised in that aldehydes of the general formula (II)

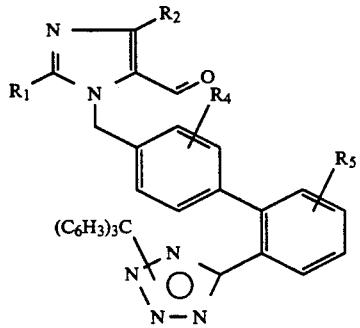

(II)

in which $R^1$, $R^2$, $R^4$ and $R^5$ have the abovementioned meaning, are reacted with phosphonoacetic acid esters of the general formula (III)

$$(R^7O)_2\text{—}P(O)\text{—}CH_2\text{—}CO_2R^7 \qquad (III)$$

in which $R^7$ has the abovementioned meaning of $R^3$, but does not represent hydrogen, in inert solvents, in the presence of a base, to give the compounds of the general formula (IV)

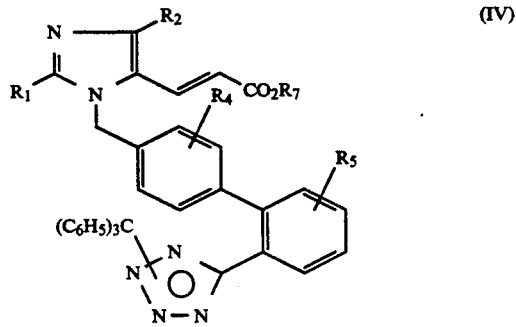

(IV)

in which $R^1$, $R^2$, $R^4$, $R^5$ and $R^7$ have the abovementioned meaning, and then the trityl group is removed with acids, and in the case of the acids ($R^3$=H) the esters are hydrolysed and in the case in which $R^6$ does not represent hydrogen, alkylated.

The process according to the invention can be illustrated by way of example by the following reaction scheme:

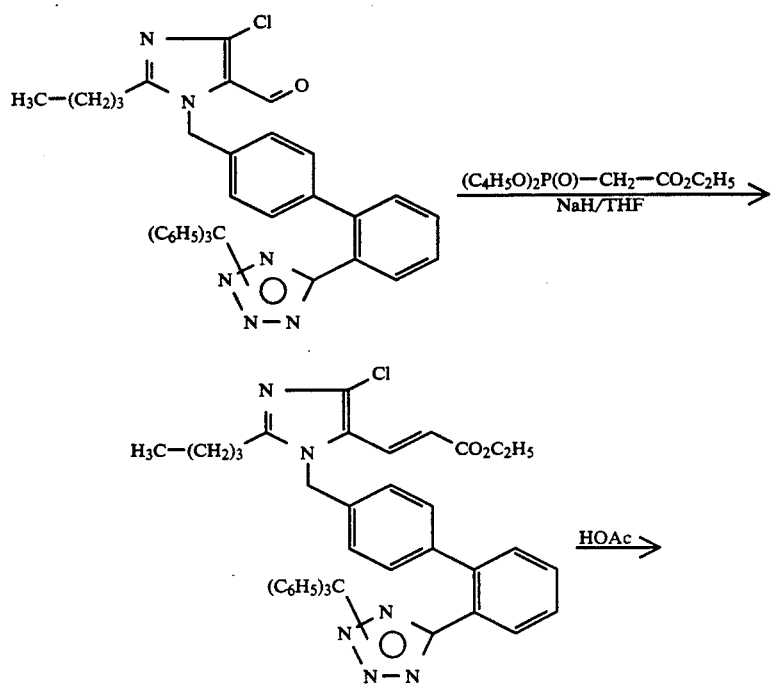

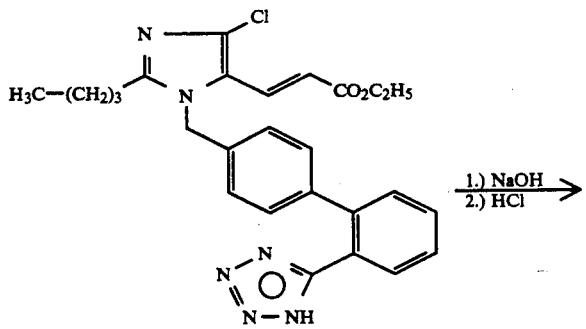

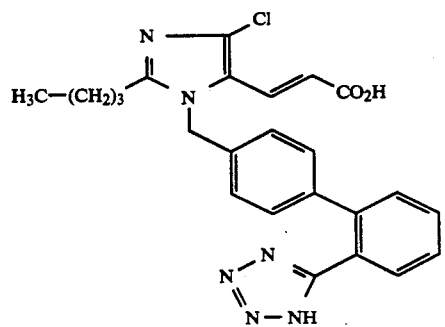

Suitable solvents for the process are the customary organic solvents which do not change under the reaction conditions. These preferably include ethers such as diethyl ether, dioxane, tetrahydrofuran, glycol dimethyl ether, and hydrocarbons such as benzene, toluene, xylene, hexane, cyclohexane or mineral oil fractions, and halogenohydrocarbons such as dichloromethane, trichloromethane, tetrachloromethane, dichloroethylene, trichloroethylene or chlorobenzene, and ethyl acetate, triethylamine, pyridine, dimethyl sulphoxide, dimethylformamide, hexamethylphosphoric triamide, acetonitrile, acetone and nitromethane. It is also possible to use mixtures of the solvents mentioned. Tetrahydrofuran is preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, and alkali metal or alkaline earth metal alkoxides such as sodium methoxide or potassium methoxide, sodium ethoxide or potassium ethoxide or potassium tert-butoxide, and organic amines (trialkyl($C_1$–$C_8$)amines) such as triethylamine, and heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals, such as sodium, or their hydrides such as sodium hydride. Sodium hydride is preferred.

In general, the base is employed in an amount from 0.05 mol to 10 mol, preferably from 1 mol to 2 mol, relative to 1 mol of the compound of the formula (III).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5 bar).

Suitable acids for the removal of the triphenylmethyl group are in general organic, optionally halogenated $C_1$–$C_6$-carboxylic acids. Glacial acetic acid and trifluoroacetic acid are preferred.

Removal is in general carried out in a temperature range from 0° C. to +120° C., preferably from +20° C. to +100° C. and at normal pressure.

Suitable bases for the hydrolysis are the customary inorganic bases. These preferably include alkali metal hydroxides and alkaline earth metal hydroxides such as, for example, sodium hydroxide, potassium hydroxide or barium hydroxide, and alkali metal carbonates such as sodium carbonate or potassium carbonate or sodium hydrogen carbonate and alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, and ethers such as tetrahydrofuran or dioxane, and dimethylformamide, and dimethyl sulphoxide. Particularly preferably, alcohols such as methanol, ethanol, propanol or isopropanol are used. It is also possible to employ mixtures of the solvents mentioned.

The hydrolysis can optionally also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Particularly preferably, molar amounts of the reactants are used.

When carrying out the reaction, in the first step the carboxylates of the compounds according to the invention are formed as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. It has proved advantageous in the preparation of the carboxylic acids in this connection to acidify the basic reaction mixture from the hydrolysis in a second step without isolation of the carboxylates. The acids can then be isolated in a customary manner. In the case of the basic heterocycles, by treatment of the solutions of the carboxylates with the abovementioned acids the salts of the heterocycles with the inorganic acids can also be obtained.

The alkylation is in general carried out using alkylating agents such as, for example, ($C_1$–$C_6$)-alkyl halides, sulphonic acid esters or substituted or unsubstituted ($C_1$–$C_6$)-dialkyl or ($C_1$–$C_6$)-diaryl sulphonates, preferably methyl iodide or dimethyl sulphate.

The alkylation is in general carried out in one of the abovementioned solvents, preferably in dimethylformamide, in a temperature range from 0° C. to +70° C., preferably from 0° C. to +30° C. and at normal pressure.

The aldehydes of the general formula (II) are known per se or can be prepared by a customary method [cf. PCT Application WO 91/002773].

The phosphonoacetic acid esters of the general formula (III) are also known [cf. Beilstein 4 (1) 573].

The compounds of the general formula (IV) are, as actual substance representatives, new and can then be prepared, for example, by the abovementioned process.

The abovementioned preparation processes are only given for clarification. The preparation of the compounds of the general formula (I) according to the invention is not restricted to these processes, and any modification of these processes is utilisable in the same manner for the preparation.

The imidazolyl-propenoic acids and derivatives according to the invention exhibit an unforeseeable, useful pharmacological spectrum of action.

The compounds according to the invention have a specific A II antagonistic action, as they competitively inhibit the binding of angiotensin II to the receptors. They suppress the vasoconstrictory and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be used for the treatment of coronary heart diseases, cardiac insufficiency, disorders of cerebral function, ischaemic brain disorders, peripheral circulatory disorders, functional disorders of the kidneys and adrenal glands, bronchospastic and vascularly conditioned disorders of the airways, sodium retention and oedemas.

Investigation of the inhibition of the contraction induced with agonists

Rabbits of both sexes are anaesthetized by a blow to the neck and bled out, or alternatively anaesthetized with Nembutal (about 60–80 mg/kg i.v.) and sacrificed by opening the thorax. The thorax aorta is taken out, freed from adhering connective tissue, divided into 1.5 Mm wide ring segments and these are individually transferred under an initial loading of about 3.5 g to 10 ml organ baths containing 95% $O_2$/5% $CO_2$-aerated Krebs-Henseleit nutrient solution thermostated at 37° C. and of the following composition: 119 mmol/l NaCl; 2.5 mmol/l $CaCl_2 \times 2H_2O$; 1.2 mmol/l $KH_2PO_4$; 10 mmol/l glucose; 4.8 mmol/l KCl; 1.4 mmol/l $MgSO_4 \times 7$ $H_2O$ and 25 mmol/l $NaHCO_3$.

The contractions are detected isometrically by Statham UC2 cells by means of a bridge amplifier (ifd Mülheim or DSM Aalen) and digitized and evaluated by means of an A/D converter (System 570, Keithley, Munich). The agonist dose-response curves (DRC) are carried out hourly. With each DRC, 3 or 4 individual concentrations are applied to the baths at 4 min intervals. After the end of the DRC and subsequent washing-out cycles (16 times, in each case about 5 sec/min with the abovementioned nutrient solution), a 28 minute resting or incubation phase follows, in the course of which the contractions as a rule again reach the starting value.

The height of, in the normal case, the 3rd DRC is used as a reference quantity for the assessment of the test substance to be investigated in further passages, which test substance is applied to the baths in increasing dose in each case at the start of the incubation time in the following DRCs. Each aorta ring is in this case stimulated for the whole day, always with the same agonist.

| Agonists and their standard concentrations (administration volume per individual dose = 100 µl): | | |
|---|---|---|
| KCl | 22.7;32.7;42.7;52.7 | mmol/l |
| 1-Noradrenaline | $3 \times 10^{-9}$;$3 \times 10^{-8}$;$3 \times 10^{-7}$; $3 \times 10^{-6}$ | g/ml |
| Serotonin | $10^{-8}$;$10^{-7}$;$10^{-6}$;$10^{-5}$ | g/ml |
| B-HT 920 | $10^{-7}$;$10^{-6}$;$10^{-5}$ | g/ml |
| Methoxamine | $10^{-7}$;$10^{-6}$;$10^{-5}$ | g/ml |
| Angiotensin II | $3 \times 10^{-9}$;$10^{-8}$;$3 \times 10^{-8}$;$10^{-7}$ | g/ml |

For the calculation of the $IC_{50}$ (concentration at which the substance to be investigated causes a 50% inhibition), the effect in each case at the 3rd=submaximal agonist concentration is used as a basis.

The compounds according to the invention inhibit the contraction of the isolated rabbit aorta induced by angiotensin II in a dose-dependent manner. The contraction induced by potassium depolarisation or other agonists was not inhibited, or only weakly inhibited at high concentrations.

TABLE A:

| Inhibition of vascular contraction in isolated aorta rings of rabbits in vitro | |
|---|---|
| $IC_{50}$ (g/ml) with respect to contractions induced by: | |
| Ex. No.: | AII |
| 1 | $2.5 \times 10^{-8}$ g/ml |
| 2 | $2.1 \times 10^{-8}$ g/ml |

Blood pressure measurements on the angiotensin II-infused rat

Male Wistar rats (Moellegaard, Copenhagen, Denmark) having a body weight of 300-350 g are anaesthetized with thiopental (100 mg/kg i.p.). After tracheotomy, one catheter is inserted in the femoral artery for blood pressure measurement and one catheter is inserted for angiotensin II infusion and one catheter is inserted for substance administration in the femoral veins. After administration of the ganglion blocker pentolinium (5 mg/kg i.v.), the angiotensin II infusion (0.3 μg/kg/min) is started. As soon as the blood pressure values have reached a stable plateau, the test substances are administered either intravenously or orally as a suspension or solution in 0.5% Tylose. The blood pressure changes under the influence of substance are indicated in the table as average values ±SEM.

Determination of the antihypertensive activity in conscious hypertensive rats

The oral antihypertensive activity of the compounds according to the invention was tested on conscious rats having surgically induced unilateral renal artery stenosis. For this, the right renal artery was constricted with a silver clip of 0.18 mm internal width. In this form of hypertension, the plasma renin activity is increased in the first six weeks after intervention. The arterial blood pressure of these animals was measured by bloodless means at defined time intervals after substance administration using the "tail cuff". The substances to be tested were administered intragastrally ("orally") by stomach tube in different doses, suspended in a Tylose suspension. The compounds according to the invention lower the arterial blood pressure of the hypertensive rats at a clinically relevant dosage.

In addition, the compounds according to the invention inhibit the specific binding of radioactive angiotensin II in a concentration-dependent manner.

Interaction of the compounds according to the invention with the angiotensin II receptor on membrane fractions of the adrenal gland cortex of cattle Adrenal gland cortices of cattle (AGC), which have been freshly removed and carefully freed from gland medulla, are comminuted in sucrose solution (0.32 M) with the aid of an Ultra-Turrax (Janke & Kunkel, Staufen i.B.) to give a coarse membrane homogenate and are partially purified in two centrifugation steps to give membrane fractions.

The receptor binding investigations are carried out on partially purified membrane fractions of bovine AGC using radioactive angiotensin II in an assay volume of 0.25 ml, which in detail contains the partially purified membranes (50-80 μg), $^3$H-angiotensin II (3-5 nM), test buffer solution (50 mM tris, pH 7.2, 5 mM MgCl$_2$, 0.25% BSA) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the total binding of the radioligand).

Investigation of inhibition of the proliferation of smooth muscle cells by the compounds according to the invention To determine the antiproliferative action of the compounds, smooth muscle cells are used which have been obtained from the aortas of rats by the media explant technique [R. Ross, J. Cell. Biol. 50, 172, 1971]. The cells are inoculated in suitable culture dishes, as a rule 24-hole plates, and cultured at 37° C. in 5% CO$_2$ for 2-3 days in medium 199 containing 7.5% FCS and 7.5% NCS, 2 mM L-glutamine and 15 mM HEPES, pH 7.4. After this, the cells are synchronised by withdrawal of serum for 2-3 days and then stimulated into growth with AII, serum or other factors. At the same time, test compounds are added. After 16-20 hours, 1 μCi of $^3$H-thymidine is added and the incorporation of this substance into the TCA-precipitable DNA of the cells is determined after a further 4 hours.

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent, if appropriate organic solvents can be used as auxiliary solvents.

Administration is carried out in a customary manner, preferably orally or parenterally, in particular perlingually or intravenously.

In the case of parenteral administration, solutions of the active substance using suitable liquid excipients can be employed.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may sometimes be necessary to depart from the amounts mentioned, in particular depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of the administration of larger amounts, it may be advisable to divide these into several individual doses over the course of the day.

Starting Compounds

EXAMPLE I 2-n-Butyl-1-[(2'-(N-triphenylmethyl-tetrazol-5-yl)biphenyl-4-yl)methyl]-1H-imidazole-5-carboxaldehyde

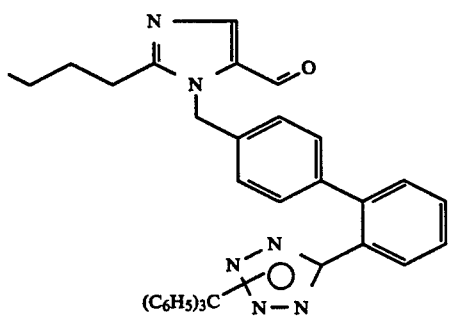

12.0 g (18.1 mmol) of 2-n-butyl-4-chloro-1-[(2'-(N-triphenylmethyltetrazol-5-yl)biphenyl-4-yl)methyl]-1H-imidazole-5-carboxaldehyde in 150 ml of methanol are hydrogenated at 25° C. for 1.5 h at a hydrogen pressure of about 3 bar in the presence of 1. 2 g of palladium on active carbon (5%) and 2.46 g (18.1 mmol) of sodium acetate trihydrate. The solution is then filtered off from the catalyst and concentrated, and the residue is chromatographed on silica gel 60 using ethyl acetate/petroleum ether (1:1).

Yield: 3.85 g (34% of theory).

$R_f$=0.41 (ethyl acetate/petroleum ether=1:1).

EXAMPLE II

Ethyl (E)-3-[2-n-butyl-4-chloro-1-{(2'-(N-triphenylmethyltetrazol-5-yl)biphenyl-4-yl)methyl}-1H-imidazol-5-yl)-2-propenoate

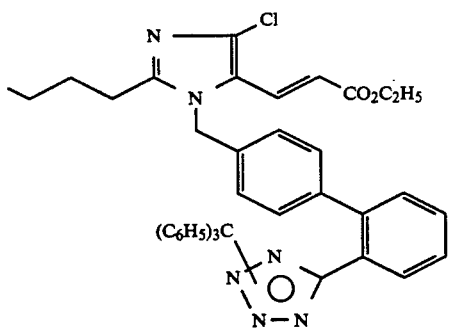

Under protective gas, 42 mg (1.2 mmol) of sodium hydride (80% strength) are suspended in 6 ml of THF, 224 mg (1.0 mmol) of triethyl phosphonoacetate are added dropwise at 25° C., the mixture is then stirred for 1 h at 25° C. and 460 mg (0.69 mmol) of 2-n-butyl-4-chloro-1-[2'-(N- triphenylmethyltetrazol-5-yl)biphenyl-4-yl-methyl]-1H-imidazole-5-carboxaldehyde are added dropwise in 4 ml of THF. The mixture is subsequently stirred for 20 h at 25° C. After concentration, the residue is partitioned between water/ethyl acetate, the organic phase is dried over sodium sulphate and concentrated, and the residue is chromatographed on silica gel 60 using ethyl acetate/petroleum ether (1:1).

Yield: 400 mg (79% of theory).

$R_f$=0.65 (ethyl acetate/petroleum ether 1:1).

EXAMPLE III

Ethyl (E)-3-[2-n-butyl-1-{(2'-(N-triphenylmethyltetrazol-5-yl)biphenyl-4-yl)methyl}-1H-imidazol-5-yl]-2-propenoate

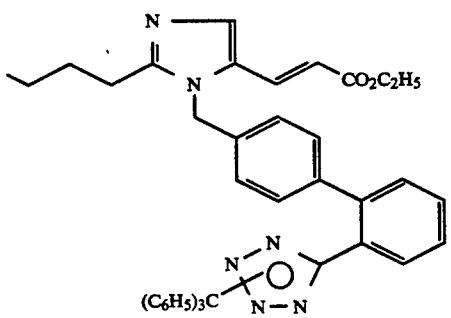

In analogy to the procedure of Example II, the title compound was prepared from 1.8 g (2.86 mmol) of the compound from Example I.

Yield: 1.31 g (66% of theory).

$R_f$=0.37 (ethyl acetate/petroleum ether=1:1).

Preparation Examples

EXAMPLE 1

Ethyl (E)-3-[2-n-butyl-4-chloro-1-{(2'-(tetrazol-5-yl)biphenyl-4-yl)methyl}-1H-imidazol-5-yl]-2-propenoate

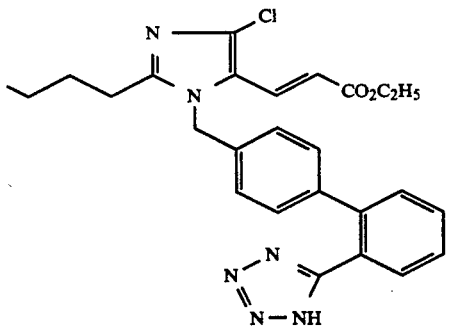

122 mg (0.166 mmol) of the compound from Example II are dissolved in 3.5 ml of glacial acetic acid. 3.5 ml of water are then added. The mixture is stirred for 2 h at 80° C. and for 20 h at 25° C. After concentration, the residue is chromatographed on silica gel 60 using dichloromethane/methanol (8:1).

Yield: 52.4 mg (64% of theory).

$R_f$=0.55 (ethyl acetate:methanol=4:1).

EXAMPLE 2

(E)-3-[2-n-Butyl-4-chloro-1-{(2'-(tetrazol-5-yl)biphenyl-4-yl)methyl}-1H-imidazol-5-yl]-2-propenoic acid

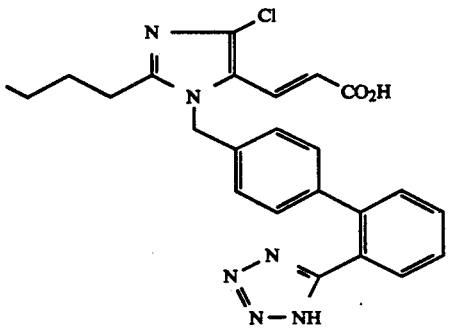

235 mg (0.32 mmol) of the compound from Example 1 are dissolved in 12 ml of 1 N methanolic sodium hydroxide solution, and the solution is heated to boiling for 30 min and stirred for 1 h at 25° C. It is acidified to pH 1 with conc. hydrochloric acid, 10 ml of ethyl acetate are added and the mixture is intensively stirred for 15 min. The organic phase is dried over sodium sulphate and concentrated, and the residue is chromatographed on silica gel 60 using ethyl acetate/methanol/ammonia=3:2:0.02.

Yield: 87 mg (59% of theory).

$R_f$=0.33 (ethyl acetate/methanol/ammonia=2:1:0.06).

EXAMPLE 3

(E)-3-[2-n-Butyl-1-{(2'-(tetrazol-5-yl)biphenyl-4-yl)methyl}-1H-imidazol-5-yl]-2-propenoic acid

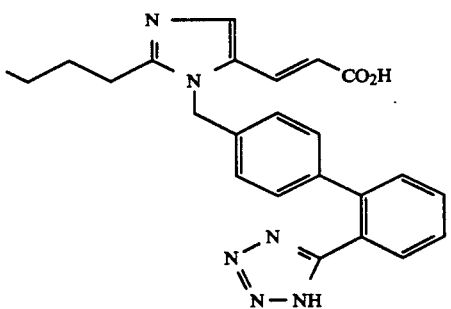

5 ml of water and 5 ml of trifluoroacetic acid are added successively to a solution of 1.3 g (1.86 mmol) of the compound from Example III in 25 ml of THF. The mixture is then stirred for 16 h at 25° C., adjusted to pH 14 with conc. sodium hydroxide solution and extracted with ether, and the aqueous phase is acidified with half-concentrated hydrochloric acid and extracted three times with 20 ml of ethyl acetate each time. The organic phase is dried over sodium sulphate and concentrated and the residue is chromatographed on silica gel 60 using dichloromethane/methanol (5:1).

Yield: 150 mg (19% of theory).

$R_f$=0.18 (dichloromethane/methanol=5:1).

What is claimed is:

1. An imidazolyl-propenoic acid derivative of the formula

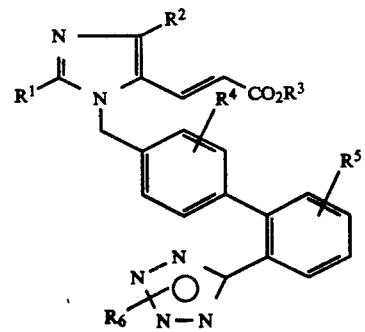

in which
   $R^1$ represents straight-chain or branched alkyl or alkenyl each having up to 8 carbon atoms, each of which is optionally substituted by cycloalkyl having 3 to 6 carbon atoms, or represents cycloalkyl having 3 to 8 carbon atoms,
   $R^2$ represents hydrogen, halogen, hydroxyl, nitro, cyano, trifluoromethyl, trifluoromethoxy or pentafluoroethyl, or represents straight-chain or branched alkyl having up to 6 carbon atoms, or represents aryl having 6 to 10 carbon atoms,
   $R^3$ represents hydrogen, straight-chain or branched alkyl having up to 8 carbon atoms or phenyl,
   $R^4$ and $R^5$ are identical or different and represent hydrogen, halogen, cyano, nitro, trifluoromethyl, hydroxyl, trifluoromethoxy or straight-chain or branched alkyl or alkoxy each having up to 6 carbon atoms,
   $R^6$ represents hydrogen or straight-chain or branched alkyl having up to 6 carbon atoms,
or a pharmaceutically acceptable salt thereof.

2. An imidazolyl-propenoic acid derivative according to claim 1 in which
   $R^1$ represents straight-chain or branched alkyl or alkenyl each having up to 6 carbon atoms, each of which is optionally substituted by cyclopropyl, cyclobutyl, cyclopentyl or cyclohexyl, or represents cyclopropyl, cyclopentyl or cyclohexyl,
   $R^2$ represents hydrogen, fluorine, chlorine, bromine, iodine, trifluoromethyl, trifluoromethoxy, pentafluoroethyl, phenyl or straight-chain or branched alkyl having up to 6 carbon atoms,
   $R^3$ represents hydrogen or straight-chain or branched alkyl having up to 6 carbon atoms,
   $R^4$ and $R^5$ are identical or different and represent hydrogen, fluorine, chlorine, bromine, trifluoromethyl, trifluoromethoxy or straight-chain or branched alkyl having up to 4 carbon atoms,
   $R^6$ represents hydrogen or straight-chain or branched alkyl having up to 4 carbon atoms,
or a pharmaceutically acceptable salt thereof.

3. An imidazolyl-propenoic acid derivative according to claim 1 in which
   $R^1$ represents straight-chain or branched alkyl or alkenyl each having up to 4 carbon atoms, or cyclopropyl,
   $R^2$ represents hydrogen, fluorine, chlorine, bromine, iodine, trifluoromethyl, pentafluoroethyl, phenyl or straight-chain or branched alkyl having up to 4 carbon atoms,
   $R^3$ represents hydrogen or straight-chain or branched alkyl having up to 4 carbon atoms, $R^4$ and $R^5$ are identical or different and represent hydrogen, fluorine, chlorine or bromine, $R^6$ represents hydrogen, methyl, ethyl, isopropyl or propyl, or a pharmaceutically acceptable salt thereof.

4. An imidazolyl-propenoic acid derivative according to claim 1 in which $R^1$ represents straight-chain or branched alkyl or alkenyl each having up to 4 carbon atoms, $R^2$ represents hydrogen, fluorine, chlorine, iodine, trifluoromethyl or pentafluoroethyl, $R^3$ represents hydrogen, methyl or ethyl and $R^4$, $R^5$ and $R^6$ represent hydrogen, or a pharmaceutically acceptable salt thereof.

5. A compound according to claim 1 wherein such compound is ethyl (E)-3-[2-n-butyl-4-chloro-1-{(2'-(tetrazol-5-yl)biphenyl-4-yl)methyl}-1H-imidazol-5-yl]-2-propenoate of the formula

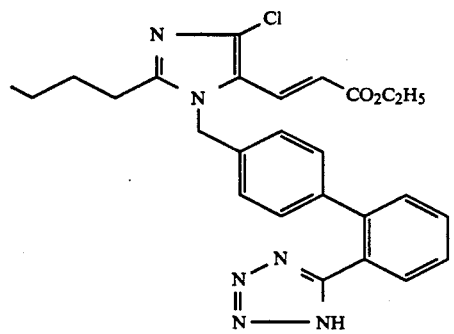

or a pharmaceutically acceptable salt thereof.

6. A compound according to claim 1 wherein such compound is (E)-3-[2-n-butyl-4-chloro-1-{(2'-(Tetrazol-5-yl)biphenyl-4-yl)methyl}-1H-imidazol-5-yl]-2-propenoic acid of the formula

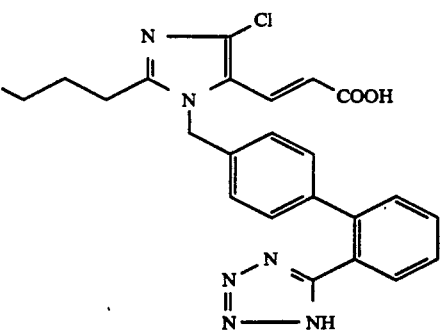

or a pharmaceutically acceptable salt thereof.

7. A compound according to claim 1 wherein such compound is (E)-3-[2-n-butyl-1-{(2'-(tetrazol-5-yl)biphenyl-4-yl)methyl}-1H-imidazol-5-yl]-2-propenoic acid of the formula

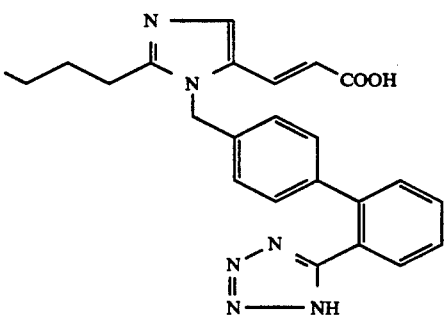

or a salt thereof.

8. Composition for the treatment of arterial hypertension and atherosclerosis comprising an amount effective therefor of a compound or pharmaceutically acceptable salt thereof according to claim 1 and a pharmacologically acceptable diluent.

9. The method of treating arterial hypertension and atherosclerosis in a patient in need thereof which comprises administering to such patient an amount effective therefor of a compound or a pharmaceutically acceptable salt thereof according to claim 1.

* * * * *

UNITED STATES PATENT AND TRADEMARK OFFICE
CERTIFICATE OF CORRECTION

PATENT NO. : 5,294,633
DATED : March 15, 1994
INVENTOR(S) : Kramer, et al.

It is certified that error appears in the above-indentified patent and that said Letters Patent is hereby corrected as shown below:

Col. 16, line 35    After " a " insert -- pharmaceutically acceptable --

Signed and Sealed this

Twelfth Day of May, 1998

Attest:

BRUCE LEHMAN

Attesting Officer    Commissioner of Patents and Trademarks